US010413352B2

(12) United States Patent
Thomas et al.

(10) Patent No.: US 10,413,352 B2
(45) Date of Patent: Sep. 17, 2019

(54) ELECTROSURGICAL INSTRUMENT

(71) Applicant: GYRUS MEDICAL LIMITED, St. Mellons, Cardiff (GB)

(72) Inventors: Daniel John Thomas, Cardiff (GB); Lewis Meurig Jones, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 807 days.

(21) Appl. No.: 14/992,193

(22) Filed: Jan. 11, 2016

(65) Prior Publication Data
US 2016/0199123 A1 Jul. 14, 2016

(30) Foreign Application Priority Data

Jan. 14, 2015 (GB) .................................. 1500532.5
Feb. 13, 2015 (GB) .................................. 1502471.4

(51) Int. Cl.
*A61B 18/14* (2006.01)
*A61B 18/00* (2006.01)
(Continued)

(52) U.S. Cl.
CPC .... *A61B 18/1445* (2013.01); *B29C 45/14475* (2013.01); *A61B 18/1442* (2013.01);
(Continued)

(58) Field of Classification Search
CPC ........ A61B 17/295; A61B 2018/00071; A61B 2018/00077; A61B 2018/00083;
(Continued)

(56) References Cited

U.S. PATENT DOCUMENTS 7,150,097 B2 12/2006 Sremcich et al.
7,473,253 B2 1/2009 Dycus et al.
(Continued)

FOREIGN PATENT DOCUMENTS

AU 2006222705 10/2006
DE 102008008309 A1 8/2009
(Continued)

OTHER PUBLICATIONS

Corrected Search Report Under Sections 17 in corresponding UK Application No. GB 1502471.4, dated Jul. 23, 2015.
(Continued)

*Primary Examiner* — Daniel W Fowler
*Assistant Examiner* — Bradford C. Blaise
(74) *Attorney, Agent, or Firm* — Oliff PLC

(57) ABSTRACT

An end effector for an electrosurgical instrument includes a pair of opposing first and second jaw members (2), (3), movable between an open position in which the jaw members are disposed in a spaced relation relative to one another, and a closed position in which sealing surfaces of the jaw members cooperate to grasp tissue therebetween. A first sealing electrode (9) is located on the first jaw member (2), while a second sealing electrode (10) is located on the second jaw member (3). One or both of the sealing surfaces are provided with electrically conductive stop members (12), the one or more stop members maintaining a predetermined spacing between the first and second sealing electrodes when the jaw members are in their closed position. One or more insulating members (14), (17), (19) are present to prevent the conductive stop members from causing an electrical short between the first and second sealing electrodes when the jaw members are in their closed position.

17 Claims, 7 Drawing Sheets

(51) Int. Cl.
*B29C 45/14* (2006.01)
*B29C 45/16* (2006.01)
*B29L 31/00* (2006.01)

(52) U.S. Cl.
CPC ............ *A61B 2018/0063* (2013.01); *A61B 2018/00071* (2013.01); *A61B 2018/00077* (2013.01); *A61B 2018/00083* (2013.01); *A61B 2018/00178* (2013.01); *A61B 2018/00607* (2013.01); *A61B 2018/00821* (2013.01); *A61B 2018/1455* (2013.01); *B29C 45/1671* (2013.01); *B29K 2995/0005* (2013.01); *B29L 2031/7546* (2013.01)

(58) Field of Classification Search
CPC .. A61B 2018/00607; A61B 2018/0063; A61B 18/1442; A61B 18/1445; A61B 2018/1455
See application file for complete search history.

(56) References Cited

U.S. PATENT DOCUMENTS

| | | |
|---|---|---|
| 7,877,852 B2 | 2/2011 | Unger et al. |
| 7,922,953 B2 | 4/2011 | Guerra |
| 8,241,284 B2 | 8/2012 | Dycus et al. |
| 2003/0014053 A1 | 1/2003 | Nguyen et al. |
| 2007/0265616 A1 | 11/2007 | Couture et al. |
| 2008/0015575 A1 | 1/2008 | Odom et al. |
| 2009/0254081 A1 | 10/2009 | Allison et al. |
| 2012/0083783 A1 | 4/2012 | Davison et al. |
| 2012/0265241 A1 | 10/2012 | Hart et al. |
| 2013/0085496 A1 | 4/2013 | Unger et al. |
| 2013/0226177 A1 | 8/2013 | Brandt et al. |
| 2013/0255063 A1 | 10/2013 | Hart et al. |
| 2014/0025073 A1 | 1/2014 | Twomey et al. |
| 2014/0194875 A1 | 7/2014 | Reschke et al. |
| 2014/0371743 A1 | 12/2014 | Rothweiler et al. |
| 2015/0018816 A1 | 1/2015 | Latimer |

FOREIGN PATENT DOCUMENTS

| | | |
|---|---|---|
| EP | 1486177 | 12/2004 |
| EP | 1795140 | 6/2007 |
| EP | 2425791 | 3/2012 |
| EP | 2687176 | 1/2014 |
| WO | 2015/197395 A1 | 12/2015 |

OTHER PUBLICATIONS

Dec. 8, 2017 Office Action issued in British Patent Application No. 1522668.1.

Combined Search and Examination Report Under Sections 17 & 18(3) in UK Application No. GB 1522668.1, dated May 26, 2016.

U.S. Appl. No. 14/992,137, filed Jan. 11, 2016, Thomas et al.
U.S. Appl. No. 14/993,408, filed Jan. 12, 2016, Thomas et al.
U.S. Appl. No. 14/993,496, filed Jan. 12, 2016, Thomas et al.
U.S. Appl. No. 14/994,464, filed Jan. 13, 2016, Jones.

Search Report in UK Application No. GB 1500532.5, dated Jun. 5, 2015.

Search Report in UK Application No. GB 1502471.4, dated Jul. 23, 2015.

Dec. 5, 2018 Office Action issued in Chinese Patent Application No. 201610021050.7.

ELECTROSURGICAL INSTRUMENT

CROSS-REFERENCE TO RELATED APPLICATION

This application claims priority to United Kingdom Application No. 1500532.5, filed 14 Jan. 2015, and United Kingdom Application No. 1502471.4, filed 13 Feb. 2015, the entire contents of each of which are incorporated herein by reference.

TECHNICAL FIELD

Embodiments of this invention relate to an electrosurgical instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to provide an electrosurgical instrument in which the sealing of tissue is effected by means of a pair of jaw elements. U.S. Pat. Nos. 7,473,253 & 8,241,284 are two examples of this kind of instrument. These two patents describe the provision of one or more non-conductive stop members, in order to regulate the spacing between the jaws when tissue is held therebetween.

SUMMARY OF THE INVENTION

Embodiments of the present invention attempt to provide an improvement to an electrosurgical instrument.

Accordingly, from one aspect an electrosurgical instrument is provided including a handle including an actuating mechanism movable between a first position and a second position, a pair of opposing first and second jaw members, the first jaw member having a first sealing surface and the second jaw member having a second sealing surface, movement of the actuating mechanism from its first position to its second position causing at least one of the jaw members to move relative to the other from a first open position in which the jaw members are disposed in a spaced relation relative to one another, to a second closed position in which the jaw members cooperate with the first and second sealing surfaces adjacent one another to grasp tissue therebetween, a first sealing electrode located on the first jaw member, a second sealing electrode located on the second jaw member, electrical connections capable of connecting the instrument to an electrosurgical generator, such that when the jaw members are in their closed position with tissue grasped therebetween, the instrument is capable of sealing the tissue by passing an electrosurgical current into the tissue from the first and second sealing electrodes, one or more electrically conductive stop members disposed on one or both of the first and second sealing surfaces, the one or more stop members maintaining a predetermined spacing between the first and second sealing electrodes when the jaw members are in their closed position, and one or more insulating members adapted to prevent the conductive stop members from causing an electrical short between the first and second sealing electrodes when the jaw members are in their closed position.

Each jaw member has a sealing surface, which is substantially planar and is the surface of the jaw which is exposed to grasp tissue therebetween. The first and second sealing electrodes form some or all of the sealing surfaces, and in some cases the first and second sealing electrodes constitute the first and second sealing surfaces. However, in other cases, the first and second sealing electrodes form only part of the first and second sealing surfaces.

The provision of electrically conductive stop members offers several advantages over the prior art instruments identified above. Firstly, this allows for the stop members to be formed from a metallic material, which is typically harder than the non-conductive materials used previously, and hence more able to regulate the spacing between the jaws in a precise manner. In contrast, non-conductive stop members tend to be formed of material which is either brittle and difficult to form (such as ceramic materials), or lacking stiffness and strength at higher temperatures (such as polymeric materials). The conductive stop members may conceivably be formed integrally as a part of the sealing electrode, as opposed to being formed as separate components as is necessary when they are non-conductive. Finally, the electrically conductive nature of the stop members provides opportunities for additional functionality, such as detecting when the jaw members are in their closed position by means of an electrical signal transmitted using the electrically conductive stop members.

According to one arrangement, the one or more electrically conductive stop members are disposed beside one or both of the first and second sealing electrodes. Conveniently, the one or more electrically conductive stop members are disposed beside the first sealing electrode, and are disposed on one or more elongate strips running longitudinally along the first sealing surface. Typically, the one or more electrically conductive stop members are disposed on two elongate strips running parallel to one another longitudinally along the first sealing surface. The one or more elongate strips preferably comprise a plurality of electrically conductive stop members. The strips provide a way of locating and spacing the stop members along the jaw member, so as to control the spacing between the sealing electrodes when the jaws members are in their closed position.

Conveniently, the plurality of electrically conductive stop members are equally spaced along the one or more elongate strips. The one or more elongate strips each preferably comprise a rail-like structure, having a length, a depth and a width, the length being greater than the depth, and the depth being greater than the width. Typically, the one or more electrically conductive stop members are disposed on the upper surface of the rail-like structure, corresponding to the length and width of the structure.

It is preferable to ensure that the one or more elongate strips are electrically insulated from the first sealing electrode. To achieve this, one or more insulating members are typically located between the one or more elongate strips and the first sealing electrode. Preferably, the one or more insulating members comprise a polymer strip running parallel to the one or more elongate strips. According to one convenient arrangement, the polymer strip is part of an overmoulded polymeric component securing the one or more elongate strips with respect to the first jaw member.

Typically, the instrument includes a knife selectively movable in a longitudinal channel in one or both of the first and second jaw members, in order to sever tissue grasped therebetween. According to a preferred arrangement, two elongate strips running parallel to one another define the longitudinal channel in which the knife is movable. The strips not only provide the one or more conductive stop members, but also define the channel in which the knife can be translated longitudinally with respect to the jaw members in order to cut tissue grasped therebetween.

Alternatively, the one or more electrically conductive stop members are disposed on one or both of the first and second sealing electrodes. According to one convenient arrangement, the one or more insulating members each comprise a pad of insulating material located opposite the or each conductive stop member on the other sealing electrode, such that the or each conductive stop member contacts the or each insulating pad when the jaw members are in their closed position. In this way, the one or more insulating pads prevent the one or more conductive stop members from causing an electrical short between the jaws when they contact each other in their closed position.

Alternatively, the one or more insulating members each conceivably comprise a continuous structure of insulating material circumnavigating an island of conductive material so as to isolate the island of conductive material from the remainder of the sealing electrode on which the structure is located. In one convenient arrangement, the one or more insulating members are each located opposite the or each conductive stop member on the other sealing electrode, such that the or each conductive stop member contacts the or each isolated island of conductive material when the jaw members are in their closed position. In this way, the area of the jaw opposite each conductive stop member is isolated from the remainder of the opposite jaw, such that contact between the conductive stop member on one jaw and the isolated island of conductive material on the other jaw does not cause an electrical short between the two jaws.

Alternatively, the one or more insulating members are conveniently each located surrounding each conductive stop member on the same sealing electrode, such that the or each conductive stop member constitutes the or each isolated island of conductive material. In this arrangement, the or each conductive stop member is electrically isolated from the remainder of the jaw on which it is located, with no requirement for the provision of any specific features on the opposite jaw member. As each stop member is isolated from the remainder of the jaw on which it is located, the closing of the jaw members will not cause an electrical short when the stop members contact the opposite sealing electrode.

Conceivably, the one or more stop members each comprise a deformation in the sealing electrode on which they are located, in order to project above the surface of the remainder of the sealing electrode. As mentioned previously, this is an advantage of the use of conductive stop members, as they can be integrally formed as a part of the electrode on which they are located. Alternatively, the one or more stop members conceivably each comprise a separate conductive member, attached to the sealing electrode on which they are located. Typically in this instance, the one or more separate conductive members are attached to the surface of the sealing electrode on which they are located.

The instrument preferably includes a plurality of conductive stop members and a plurality of insulating members. This allows for the spacing between the jaw members to be regulated along the length thereof, as opposed to merely at one specific location. Typically, the first sealing electrode includes a plurality of conductive stop members, and the second sealing electrode includes a plurality of insulating members. Alternatively or additionally, the second sealing electrode includes a plurality of conductive stop members, and the first sealing electrode includes a plurality of insulating members. Conceivably, the first sealing electrode includes both a plurality of conductive stop members and a plurality of insulating members, and the second sealing electrode includes both a plurality of conductive stop members and a plurality of insulating members. In this way, conductive stop members are provided on both jaws, along with the insulating members to prevent shorting between the jaws.

While the provision of the one or more stop members is primarily to assist in the effective sealing of tissue, the instrument typically also includes a knife selectively movable from a first position relative to the first and second jaw members to a second position relative to the first and second jaw members, in order to sever tissue grasped therebetween. In this way, the instrument is capable of grasping tissue, sealing it, and then severing the sealed tissue to form a tissue cut without bleeding.

Embodiments of the invention further reside in an end effector for an electrosurgical instrument including
  a pair of opposing first and second jaw members, the first jaw member having a first sealing surface and the second jaw member having a second sealing surface, at least one of the jaw members being movable relative to the other from a first open position in which the jaw members are disposed in a spaced relation relative to one another, to a second closed position in which the jaw members cooperate with the first and second sealing surfaces adjacent one another to grasp tissue therebetween,
  a first sealing electrode located on the first sealing surface,
  a second sealing electrode located on the second sealing surface,
  one or more electrically conductive stop members disposed on one or both of the first and second sealing surfaces, the one or more stop members maintaining a predetermined spacing between the first and second sealing electrodes when the jaw members are in their closed position, and
  one or more insulating members adapted to prevent the conductive stop members from causing an electrical short between the first and second sealing electrodes when the jaw members are in their closed position.

Embodiments of the invention further reside in a method for manufacturing a jaw member for an electrosurgical instrument, comprising the steps of:
  providing an electrically conductive plate with a longitudinally extending slot therein;
  providing a pair of elongate strips, the elongate strips containing one or more electrically conductive stop members,
  placing the electrically conductive plate and the elongate strips into a first mould, with the elongate strips being located in the longitudinally extending slot;
  injecting a first flowable insulating material into the mould;
  allowing the first flowable insulating material to solidify, such that the flowable material forms an insert containing the electrically conductive plate and the elongate strips;
  providing a jaw housing having a longitudinal jaw section;
  placing the insert and the jaw housing into a second mould;
  injecting a second flowable insulating material into the mould to secure the insert with respect to the jaw housing;
  allowing the second flowable insulating material to solidify; and
  removing the jaw housing, insert and the solidified insulating material from the mould as a jaw member.

BRIEF DESCRIPTION OF THE DRAWINGS

Embodiments of the invention will now be further described, by way of example only, with reference to the accompanying drawings, in which.

DESCRIPTION OF THE EMBODIMENTS

Figure 1:
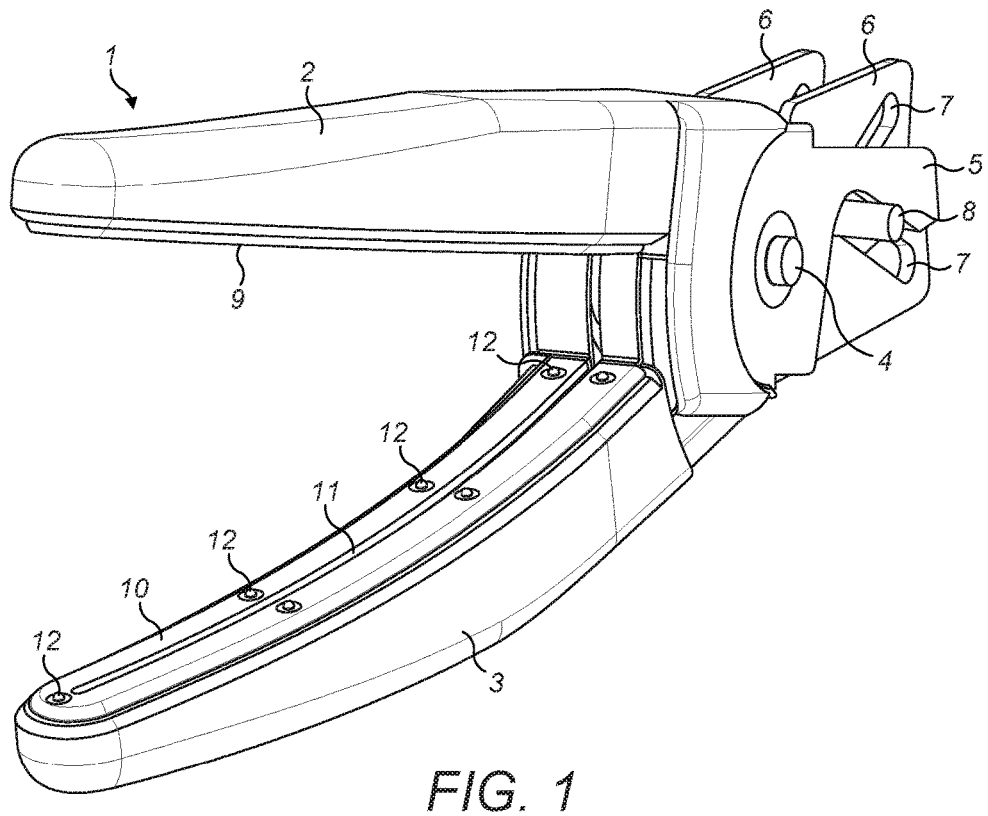
FIG. 1 is a schematic perspective view of an end effector in accordance with an embodiment of the present invention.
Figure 2:
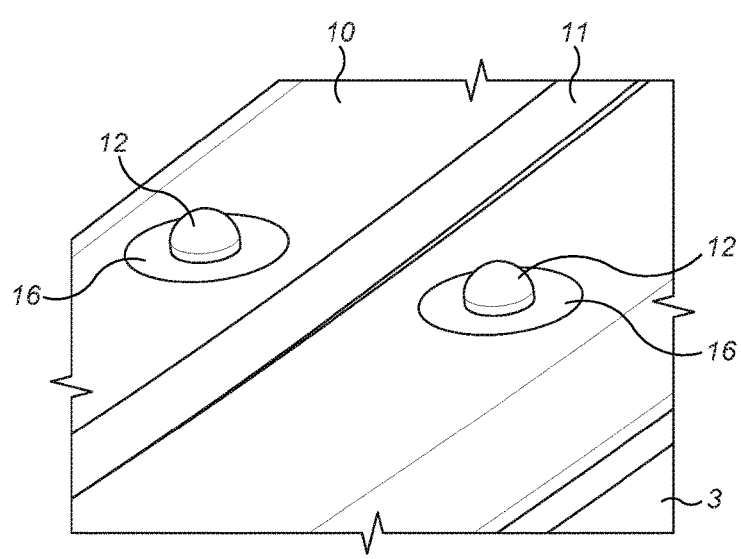
FIG. 2 is an enlarged perspective view of a part of the end effector of FIG. 1.

FIGS. 1 to 7 show example instruments where the electrically conductive stop members are disposed on one or both of the sealing electrodes. Referring to FIG. 1, an end effector shown generally at 1 comprises an upper jaw 2 pivotably connected to a lower jaw 3 about a pivot 4. Flanges 5 are present at the proximal end of upper jaw 2, while flanges 6 are present at the proximal end of lower jaw 3. The flanges 5 & 6 each have slots 7 through which a drive pin 8 extends, such that proximal and distal movement of the drive pin 8 (by means of a drive mechanism (not shown) causes the jaws 2 & 3 to pivot between open and closed positions.

A metallic shim 9 is present on the inward face of upper jaw 2, while a metallic shim 10 is present on the inward face of lower jaw 3. When the jaws 2 & 3 pivot into their closed position, the metallic shims 9 & 10 come into close proximity one with the other, in order to grasp tissue (not shown) therebetween.

The upper shim 9 has a generally planar surface, with the exception of a longitudinal groove (not visible in FIG. 1) running the length thereof. The lower shim 10 has a corresponding groove 11, the grooves in the shims 9 & 10 accommodating the longitudinal movement of a cutting blade (not shown). The lower shim 10 is also provided with a plurality of metallic stop members 12, disposed along the length of the shim and situated on either side of the groove 11. The stop members 12 will now be described in more detail, with reference to FIGS. 2 & 3.

Each metallic stop member 12 is constituted by the upper dome of a stop element 13, which is enclosed in an insulating member 14 such that it encapsulates the stop element isolating it from the remainder of the shim 10. Each insulating member 14 and stop element 13 is positioned in a corresponding aperture 15 present within the shim 10, such that the upper portion of the insulating member forms an insulating ring 16 around each stop member 12.

Figure 3:
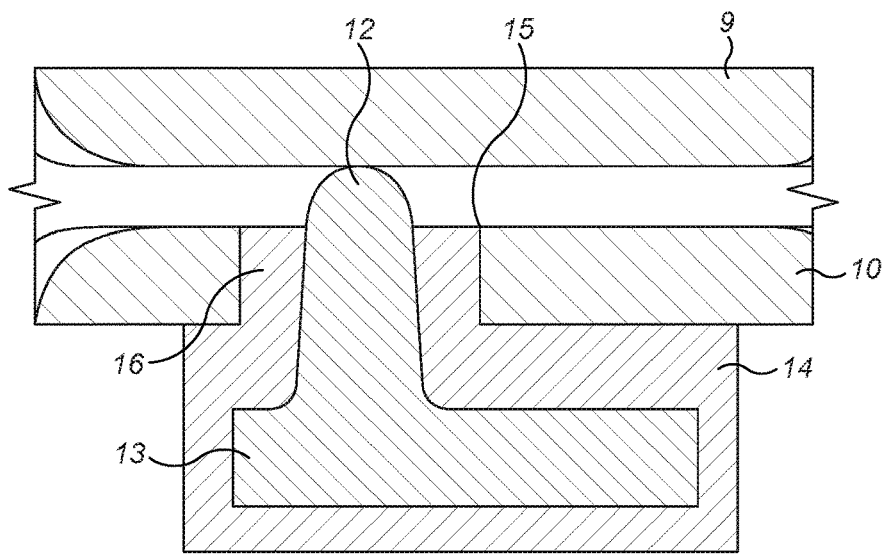
FIG. 3 is a schematic sectional view of a part of the end effector of FIG. 1.

When the jaws 2 & 3 are moved to their closed position (as shown in FIG. 3), the stop members 12 contact the upper shim 9 maintaining a separation between the upper and lower shims of between 20 μm and about 350 μm (0.00079 inches to about 0.014 inches). In use, a coagulating electrosurgical voltage is supplied between the shims 9 & 10, and the separation of the shims ensures effective sealing of tissue grasped between the jaw members 2 & 3. In the meantime, electrical shorting between the shims is prevented, as the stop members 12 are electrically isolated such they do not carry the same electric potential as the remainder of the shim 10. The metallic stop members 12 are rigid, allowing for a consistent separation of the shim surfaces, while it is feasible that the electric potential of the stop elements 13 can be monitored in order to detect when they contact the upper shim 9 to give an indication of the closure of the jaws.

Figure 4:
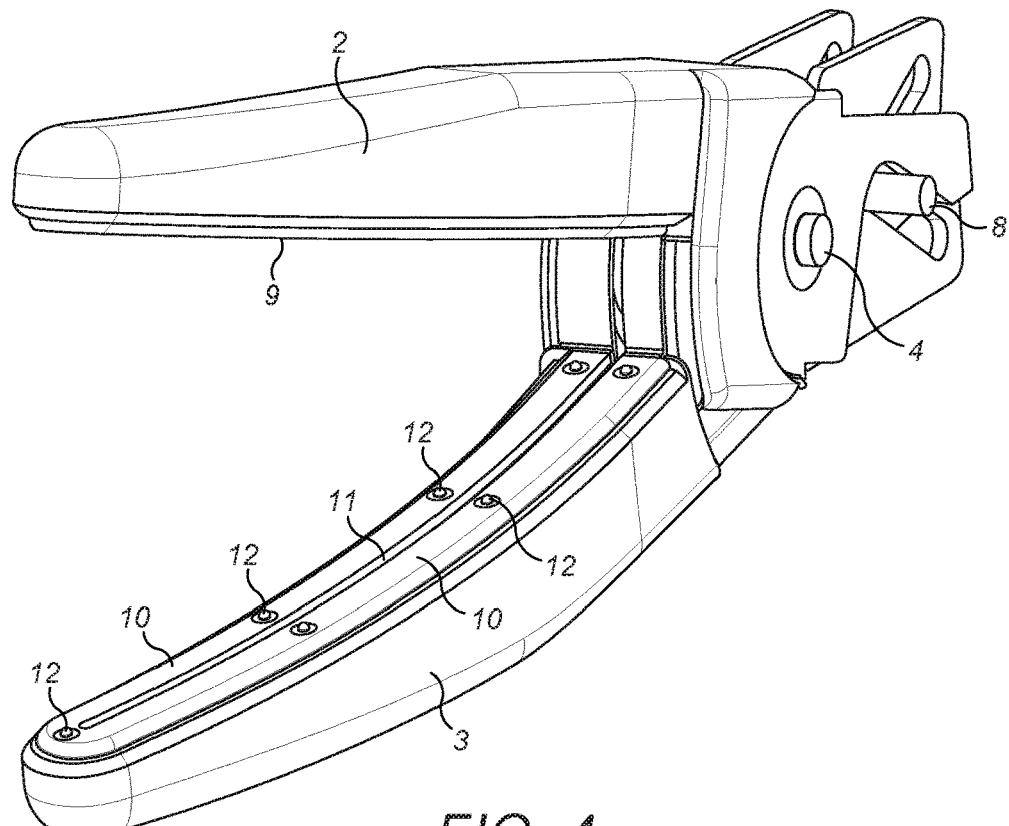
FIG. 4 is a schematic perspective view of an end effector in accordance with an alternative embodiment of the present invention.
Figure 5:
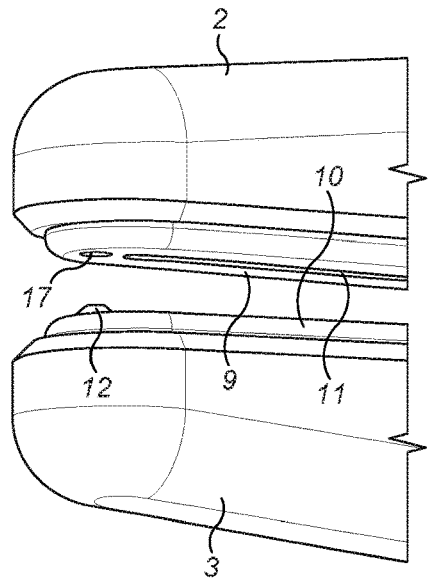
FIG. 5 is an enlarged perspective view of a part of the end effector of FIG. 4.
Figure 6:
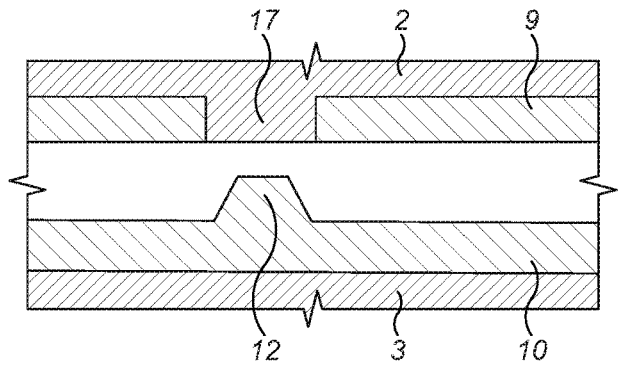
FIG. 6 is a schematic sectional view of a part of the end effector of FIG. 4.

FIGS. 4 to 6 show an alternative arrangement in which the metallic stop members 12 are mounted directly on the lower shim 10, without the provision of the insulating members surrounding the stop members. In this arrangement, insulating members 17 are provided on the upper shim 9, in corresponding relationship to each of the stop members. In this way, when the jaws 2 & 3 are closed, the insulating members 17 ensure that there is no electrical shorting between the upper shim 9 and the lower shim 10. The metallic stop members 12 ensure that the appropriate separation of the jaw members is maintained during the application of electrosurgical energy in order to seal tissue grasped between the jaws.

Figure 7:
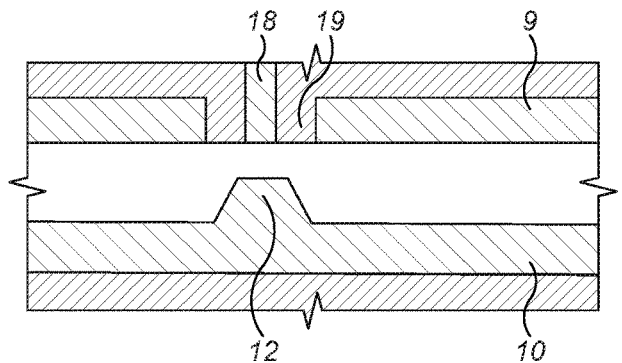
FIG. 7 is a schematic sectional view of a part of a further alternative embodiment of end effector in accordance with an embodiment of the present invention.

FIG. 7 shows a further alternative, in which the metallic stop members 12 are once again mounted directly on the lower shim 10. In this arrangement, a metallic anvil 18 is located opposite each of the stop members, each metallic anvil 18 being surrounded by an insulating member 19 in order to isolate it from the remainder of the upper shim 9. When the jaws are closed, metal-to-metal contact takes place between the stop members 12 and the metallic anvils 18, with the isolation of the anvils ensuring that electrical shorting between the shims 9 & 10 is once again avoided. Once again, the electric potential of each of the metallic anvils can be monitored in order to detect when they assume the potential of the lower shim, indicating closure of the jaws.

Figure 8:
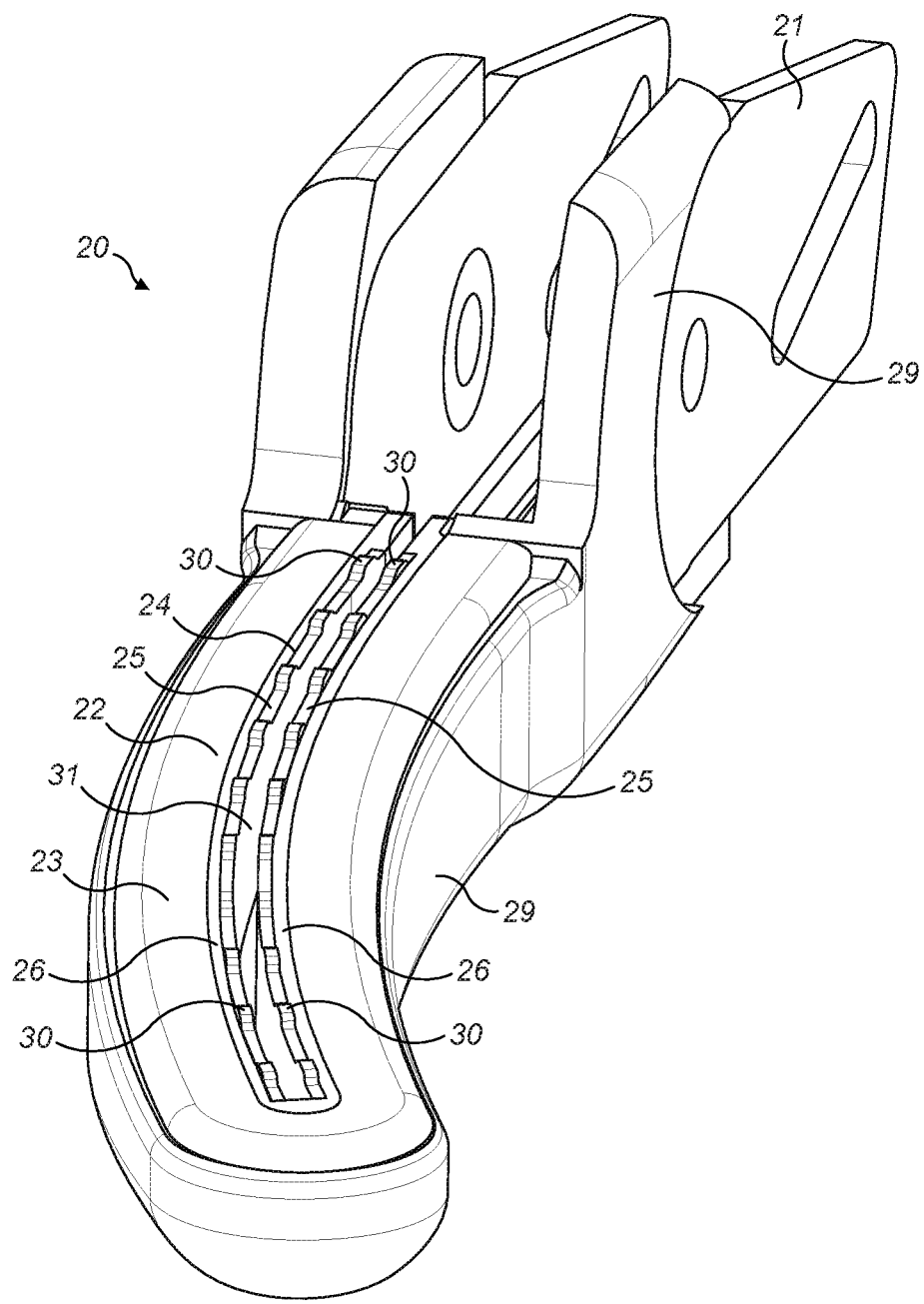
FIG. 8 is a schematic perspective view of an end effector in accordance with an alternative embodiment of the present invention.
Figure 9:
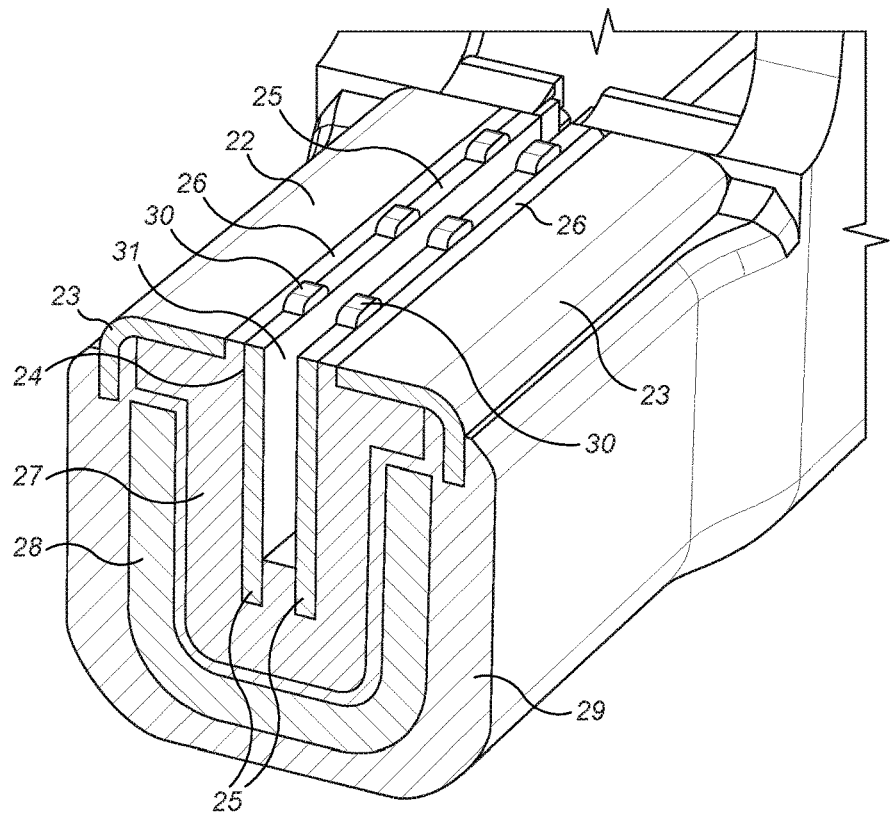
FIG. 9 is a schematic sectional view of a part of the end effector of FIG. 8.
Figure 10:
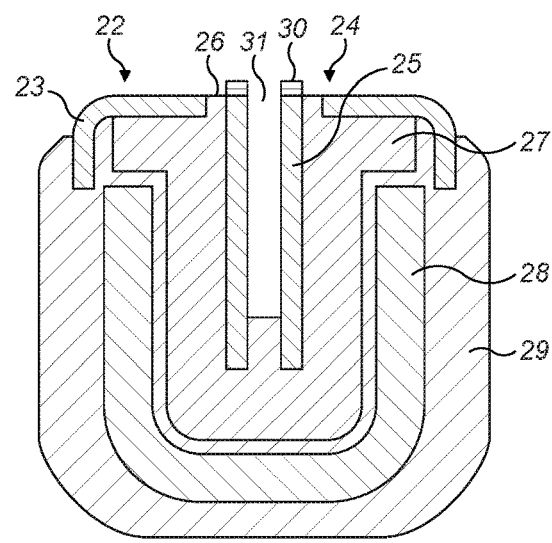
FIG. 10 is an enlarged sectional view of the end effector of FIG. 9.

FIGS. 8 to 15 show an example instrument where the electrically conductive stop members are disposed beside the sealing electrode on one of the sealing surfaces. FIG. 8 shows a lower jaw 20 with flanges 21 at its proximal end, as previously described. The jaw 20 has a planar sealing surface 22 constituted in the main by a metallic shim 23 similar in part to that of the jaw of FIG. 1. The shim 23 has a central slot 24, in which is located two metallic tracks 25. The tracks run longitudinally within the slot 24, and are separated from the shim 23 by a border 26 of insulating material, protruding up into the slot as part of a polymer moulding 27, shown more clearly with respect to FIGS. 9 & 10.

The polymer moulding 27 is located on a metallic jaw frame 28, and secured in place by means of an overmoulded jaw body 29. The upper edges of the metallic tracks 25 are provided with metallic stop members 30, arranged in pairs and equally spaced along the upper edges of the tracks 25. The inner faces of the tracks define a channel 31 to accommodate the longitudinal movement of a cutting blade (not shown). In use, the jaw 20 closes against an upper jaw (not shown, but similar to the jaw 2 shown in FIG. 1), with the stop members 30 contacting the upper shim 9 (as shown in FIG. 1). The stop members 30 control the spacing between the upper jaw 9 and the lower jaw 20, as previously described. As the metallic tracks 25 are isolated from the shim 23 by means of the polymer border 26, shorting between the shims on the upper and lower jaws is prevented.

Figure 11:
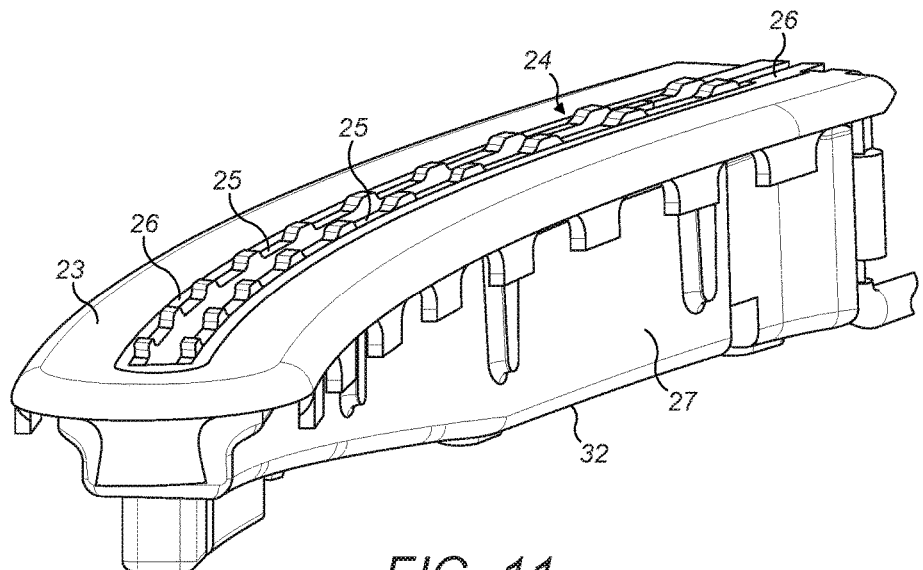
FIG. 11 is a schematic perspective view of a subcomponent formed during the manufacture of the end effector of FIG. 8.

The method of manufacture of the jaw 20 is shown in FIGS. 11 to 15. Firstly, the shim 23 is placed in a mould (not shown) and the tracks 25 are placed in the central slot 24 of the shim. A flowable polymer material is used to create an overmoulded sub-assembly 32, securing the shim 23 and the tracks 25 in position. The overmoulded polymer material flows between the tracks 25 and the shim 23 to create the insulating border 26. This is the component as shown in FIG. 11.

Figure 12:
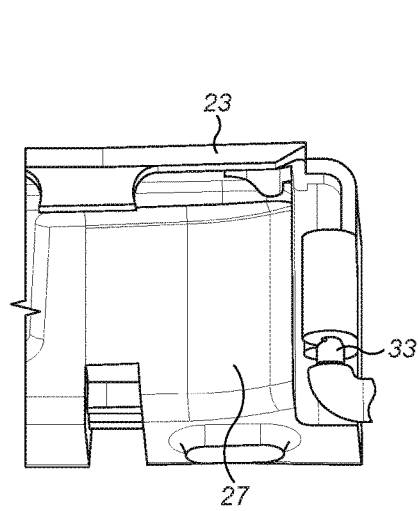
FIG. 12 is an enlarged side view of a part of the subcomponent of FIG. 11.
Figure 13:
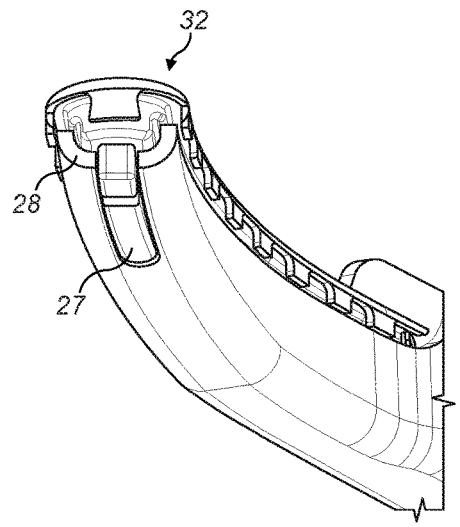
FIG. 13 is a schematic perspective view of a further subcomponent formed during the manufacture of the end effector of FIG. 8, and FIGS. 14 and 15 are schematic views of an alternative component used during the manufacture of the end effector of FIG. 8.

A wire 33 is secured to the shim 23 and crimped in position as shown in FIG. 12. This constitutes the electrical supply to the shim 23 when the shim is acting as a sealing electrode. Then the sub-assembly 32 is placed on the jaw frame 28 as shown in FIG. 13 and the assembly is placed in a further mould (not shown). A flowable polymer material is introduced into the mould in order to create the final overmoulded jaw, as shown in FIG. 8, with the outer overmoulded component being shown at 29.

Figure 14:
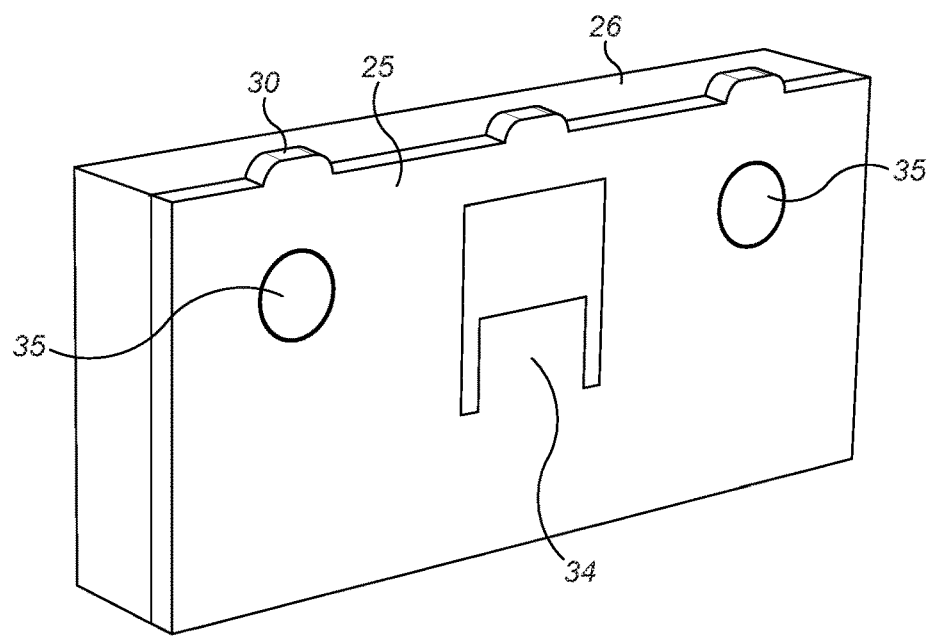
Figure 15:
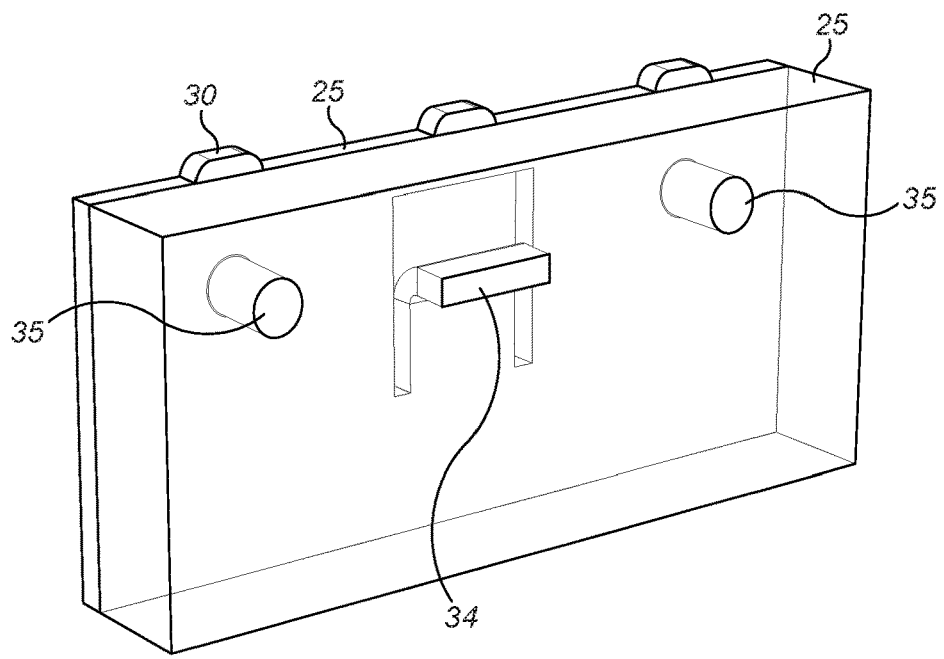

The tracks 25 are held in position with respect to the rest of the jaw 20 by means of the overmoulded polymer moulding 27. However, if additional mechanical integrity is required, the tracks 25 can be provided with lugs 34 or pins 35 for additional attachment between the tracks 25 and the polymer moulding 27. These arrangements are shown in FIGS. 14 & 15.

Other methods of providing conductive stop members are available as an alternative to the metallic tracks 25. For example, discrete metallic pegs can be received in holes provided in the polymer moulding 27. Those skilled in the art will appreciate that other possible assembly methods are available for providing metallic stop members insulated from the shim on or beside which they are located.

Additional or alternative functionality available for the use of conductive stop members includes measuring the electrical resistance between the conductive stop member and the electrically conductive shim on which it is mounted. This provides an indication of the presence or absence of tissue between the jaws. Alternatively, the electrical resistance between the conductive stop member and the shim on the opposite jaw can be measured. This gives an indication of the spacing between the jaws. Conceivably, the electrically conductive stop members could form part of a thermocouple arrangement, to give an indication of the tissue temperature at various locations along the jaws.

Whichever arrangement is employed, the provision of electrically conductive stop members ensures that the jaw spacing is regulated effectively, with rigid metal-to-metal contact being possible to provide a precise and sturdy structure. In addition, the electrical conductivity of the stop members allows for increased functionality, with various measurements possible using the electrically conductive nature of the stop members.

The invention claimed is:

1. An electrosurgical instrument comprising:
   a handle including an actuating mechanism movable between a first position and a second position;
   a first jaw member and a second jaw member, the first jaw member having a first inner surface and the second jaw member having a second inner surface, movement of the actuating mechanism from its first position to its second position causing at least one of the first jaw member and the second jaw member to move relative to the other from a first open position in which the first jaw member and the second jaw member are disposed in a spaced relation relative to one another, to a second closed position in which the first jaw member and the second jaw member cooperate with the first inner surface and the second inner surface adjacent one another;
   a first sealing electrode located on the first inner surface of the first jaw member:
   a second sealing electrode located on the second inner surface of the second jaw member:
   electrical connections capable of connecting the instrument to an electrosurgical generator, such that when the first jaw member and the second jaw member are in their second closed position with tissue grasped therebetween, the instrument is capable of sealing the tissue by passing an electrosurgical current into the tissue from the first sealing electrode and the second sealing electrode;
   an electrically conductive stop member disposed on one or both of the first inner surface of the first jaw member and the second inner surface of the second jaw member, the electrically conductive stop member maintaining a predetermined spacing between the first sealing electrode and the second sealing electrode when the first jaw member and the second jaw member are in their second closed position, wherein the electrically conductive stop member is disposed on an elongate stop element, the elongate stop element (1) being separate from the first sealing electrode and the second sealing electrode and (2) having a dimension greater than that of a corresponding electrically conductive stop member; and
   an insulating member surrounding the electrically conductive stop member and the elongate stop element such that the electrically conductive stop member and the elongate stop element are embedded in the insulating member, wherein the insulating member comprises a continuous structure of insulating material circumnavigating the electrically conductive stop member so as to isolate the electrically conductive stop member from the remainder of the sealing electrode on which the structure is located, the insulating member being configured to prevent the electrically conductive stop member from causing an electrical short between the first sealing electrode and the second sealing electrode when the first jaw member and the second jaw member are in their second closed position.

2. The electrosurgical instrument according to claim 1, wherein the electrically conductive stop member is disposed beside one or both of the first sealing electrode and the second sealing electrode.

3. The electrosurgical instrument according to claim 2, wherein the electrically conductive stop member is disposed beside the first sealing electrode.

4. The electrosurgical instrument according to claim 3, wherein the elongate stop element comprises an elongate strip running longitudinally along the first inner surface of the first jaw member, the electrically conductive stop member being disposed on the elongate strip.

5. The electrosurgical instrument according to claim 4, including a plurality of electrically conductive stop members.

6. The electrosurgical instrument according to claim 4, wherein the electrically conductive stop member comprises a plurality of electrically conductive stop members disposed on two elongate strips running parallel to one another longitudinally along the first inner surface of the first jaw member.

7. The electrosurgical instrument according to claim 5, wherein the plurality of electrically conductive stop members are equally spaced along the elongate strip.

8. The electrosurgical instrument according to claim 4, wherein the elongate strip comprises a rail having a length, a depth and a width, the length being greater than the depth, and the depth being greater than the width.

9. The electrosurgical instrument according to claim 8, wherein the rail includes an upper surface, and the electrically conductive stop member is disposed on the upper surface of the rail.

10. The electrosurgical instrument according to claim 4, wherein the insulating member is located between the elongate strip and the first sealing electrode.

11. The electrosurgical instrument according to claim 10, wherein the insulating member comprises a polymer strip running parallel to the elongate strip.

12. The electrosurgical instrument according to claim 11, wherein the polymer strip is part of an overmoulded polymeric component securing the elongate strip with respect to the first jaw member.

13. The electrosurgical instrument according to claim 1, wherein the electrosurgical instrument includes a knife selectively movable in a longitudinal channel in one or both of the first jaw member and the second jaw member, in order to sever tissue grasped therebetween.

14. The electrosurgical instrument according to claim 6, wherein the electrosurgical instrument includes a knife selectively movable in a longitudinal channel in one or both of the first jaw member and the second jaw member, in order to sever tissue grasped therebetween, wherein the two elongate strips running parallel to one another define the longitudinal channel in which the knife is movable.

15. The electrosurgical instrument according to claim 1, wherein the electrically conductive stop member comprises a plurality of electrically conductive stop members positioned in corresponding apertures within at least one of the first sealing electrode and the second sealing electrode.

16. The electrosurgical instrument according to claim 15, wherein the instrument includes a knife selectively movable from a first position relative to the first jaw member and the second jaw member to a second position relative to the first jaw member and the second jaw member, in order to sever tissue grasped therebetween.

17. An end effector for an electrosurgical instrument including
 a first jaw member and a second jaw member, the first jaw member having a first inner surface and the second jaw member having a second inner surface, at least one of the first jaw member and the second jaw member being movable relative to the other from a first open position in which the first jaw member and the second jaw member are disposed in a spaced relation relative to one another, to a second closed position in which the jaw members cooperate with their inner surfaces adjacent one another,
 a first sealing electrode located on the first inner surface of the first jaw member,
 a second sealing electrode located on the second inner surface of the second jaw member,
 an electrically conductive stop member disposed on one or both of the first inner surface of the first jaw member and the second inner surface of the second jaw member, the electrically conductive stop member maintaining a predetermined spacing between the first sealing electrode and the second sealing electrode when the first jaw member and the second jaw member are in their second closed position, wherein the electrically conductive stop members is disposed on an elongate stop element having a dimension greater than that of a corresponding electrically conductive stop member, and
 an insulating member contacting and surrounding the electrically conductive stop member and the elongate stop element such that the electrically conductive stop member and the elongate stop element are embedded in the insulating member, wherein the insulating member comprises a continuous structure of insulating material circumnavigating the electrically conductive stop member so as to isolate the electrically conductive stop member from the remainder of the sealing electrode on which the structure is located, the insulating member being configured to prevent the electrically conductive stop member from causing an electrical short between the first sealing electrode and the second sealing electrode when the first jaw member and the second jaw member are in their second closed position.

* * * * *